United States Patent
Moffitt et al.

(10) Patent No.: US 10,156,476 B2
(45) Date of Patent: Dec. 18, 2018

(54) SOLID STATE WIDEBAND FOURIER TRANSFORM INFRARED SPECTROMETER

(71) Applicant: BAE SYSTEMS Information & Electronic Systems Integration Inc., Nashua, NH (US)

(72) Inventors: Paul R Moffitt, Hollis, NH (US); Peter A Ketteridge, Amherst, NH (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 312 days.

(21) Appl. No.: 14/825,839

(22) Filed: Aug. 13, 2015

(65) Prior Publication Data
US 2016/0377482 A1    Dec. 29, 2016

Related U.S. Application Data

(60) Provisional application No. 62/079,185, filed on Nov. 13, 2014.

(51) Int. Cl.
*G01J 3/02* (2006.01)
*G01J 3/453* (2006.01)
(Continued)

(52) U.S. Cl.
CPC .......... *G01J 3/453* (2013.01); *G01B 9/02015* (2013.01); *G01J 3/0205* (2013.01);
(Continued)

(58) Field of Classification Search
CPC .................................................. G01J 3/0205
See application file for complete search history.

(56) References Cited

U.S. PATENT DOCUMENTS

| | | | | |
|---|---|---|---|---|
| 4,799,797 A | * | 1/1989 | Huggins | G01D 5/35383 |
| | | | | 250/227.27 |
| 4,928,007 A | * | 5/1990 | Furstenau | G02F 7/00 |
| | | | | 250/227.14 |

(Continued)

OTHER PUBLICATIONS

Bahaa E. A. Saleh, Malvin Carl Teich, Nonlinear Optics, Fundamentals of Photonics, Chapter 21, pp. 773-917, John Wiley & Sons.
(Continued)

*Primary Examiner* — David Porta
*Assistant Examiner* — Djura Malevic
(74) *Attorney, Agent, or Firm* — Maine Cernota & Rardin

(57) ABSTRACT

A compact, low cost FTIR spectrometer with no moving parts includes an interferometer having optical paths through silicon waveguides. The optical path lengths are varied by changing the temperature and/or carrier density of at least one of the waveguides. In embodiments, the interferometer is a Mach-Zehnder interferometer. Embodiments vary both optical path lengths in opposite directions. In embodiments, a germanium or InGaAs IR detector is grown on the same wafer as the waveguides. Embodiments include a laser pump, such as a COT CW diode laser, and wavelength mixer, such as an OPGaAs or OPGaP converter, for up and/or down converting measured IR wavelengths into a range compatible with the waveguide and detector materials. The wavelength mixer can be a waveguide. Embodiments include a sample compartment and an IR source such as a glowbar. In embodiments, the sample compartment can be exposed to ambient atmosphere for analysis of gases contained therein.

17 Claims, 3 Drawing Sheets

(51) Int. Cl.
*G01J 3/10* (2006.01)
*G01N 21/3504* (2014.01)
*G01B 9/02* (2006.01)
*G01N 21/35* (2014.01)

(52) U.S. Cl.
CPC .......... *G01J 3/108* (2013.01); *G01N 21/3504* (2013.01); *G01N 2021/3595* (2013.01)

(56) References Cited

U.S. PATENT DOCUMENTS

| | | | | | |
|---|---|---|---|---|---|
| 4,989,979 | A | * | 2/1991 | Buckman | G01D 5/35303 250/227.27 |
| 5,082,342 | A | * | 1/1992 | Wight | G02F 1/025 372/44.01 |
| 5,117,471 | A | * | 5/1992 | Furstenau | G02F 3/022 250/227.19 |
| 5,239,598 | A | * | 8/1993 | Wight | G02F 1/025 257/431 |
| 5,508,804 | A | * | 4/1996 | Furstenau | G01B 11/18 356/35.5 |
| 5,604,581 | A | * | 2/1997 | Liu | G01B 11/0625 356/632 |
| 5,757,986 | A | * | 5/1998 | Crampton | G02F 1/025 385/131 |
| 6,233,070 | B1 | * | 5/2001 | Lu | G02F 1/2257 359/9 |
| 6,242,739 | B1 | * | 6/2001 | Cherkassky | G01B 11/0641 250/339.08 |
| 7,361,501 | B2 | * | 4/2008 | Koo | B82Y 30/00 435/287.2 |
| 7,518,728 | B2 | * | 4/2009 | Koo | G01J 3/44 356/456 |
| 7,901,870 | B1 | * | 3/2011 | Wach | G02B 5/285 430/321 |
| 7,903,338 | B1 | * | 3/2011 | Wach | A61B 5/0084 359/588 |
| 8,154,792 | B1 | * | 4/2012 | Weyburne | G02F 1/3544 359/332 |
| 2001/0031110 | A1 | * | 10/2001 | Imajuku | G02F 1/3517 385/15 |
| 2001/0050793 | A1 | * | 12/2001 | Harpin | H04B 10/506 398/141 |
| 2003/0071216 | A1 | * | 4/2003 | Rabolt | G01J 3/02 250/339.02 |
| 2004/0033004 | A1 | * | 2/2004 | Welch | B82Y 20/00 385/14 |
| 2004/0195511 | A1 | * | 10/2004 | Elmore | G01J 3/02 250/339.02 |
| 2005/0157305 | A1 | * | 7/2005 | Yu | G01D 5/35303 356/480 |
| 2006/0045445 | A1 | * | 3/2006 | Watanabe | G02F 1/3515 385/122 |
| 2007/0076208 | A1 | * | 4/2007 | Koo | G01J 3/44 356/451 |
| 2007/0077595 | A1 | * | 4/2007 | Koo | B82Y 30/00 435/7.1 |
| 2007/0221848 | A1 | * | 9/2007 | Johnson | G01J 3/02 250/339.02 |
| 2007/0274726 | A1 | * | 11/2007 | Lehmann | H04J 14/08 398/102 |
| 2008/0037608 | A1 | * | 2/2008 | Zhou | G01N 21/4795 372/50.11 |
| 2008/0204747 | A1 | * | 8/2008 | Emmerson | G01N 21/774 356/328 |
| 2008/0259969 | A1 | * | 10/2008 | Piper | H01S 3/1086 372/3 |
| 2009/0078963 | A1 | * | 3/2009 | Khodja | G02B 6/12007 257/189 |
| 2009/0231686 | A1 | * | 9/2009 | Atkins | G02B 6/12002 359/341.3 |
| 2010/0110443 | A1 | * | 5/2010 | Cheben | G01J 3/02 356/454 |
| 2011/0176768 | A1 | * | 7/2011 | Singh | G02B 5/285 385/30 |
| 2012/0162748 | A1 | * | 6/2012 | Fermann | G02F 1/353 359/330 |
| 2012/0182552 | A1 | * | 7/2012 | Heidrich | G01N 21/7746 356/364 |
| 2012/0205352 | A1 | * | 8/2012 | Fermann | H01S 3/06725 219/121.67 |
| 2012/0206726 | A1 | * | 8/2012 | Pervez | G01J 3/02 356/402 |
| 2014/0270629 | A1 | * | 9/2014 | Dutt | G02B 6/43 385/14 |
| 2014/0294338 | A1 | * | 10/2014 | Long | G02F 1/0126 385/8 |
| 2017/0131122 | A1 | * | 5/2017 | Harpin | G01D 5/35329 |

OTHER PUBLICATIONS

Kai-Daniel Büchter, Hybrid Up-Conversion Detector for Mid-Infrared Radiation using Ti:PPLN Waveguides, ECIO 2010, Cambridge, Apr. 7-9, 2010, paper ThF3.

* cited by examiner

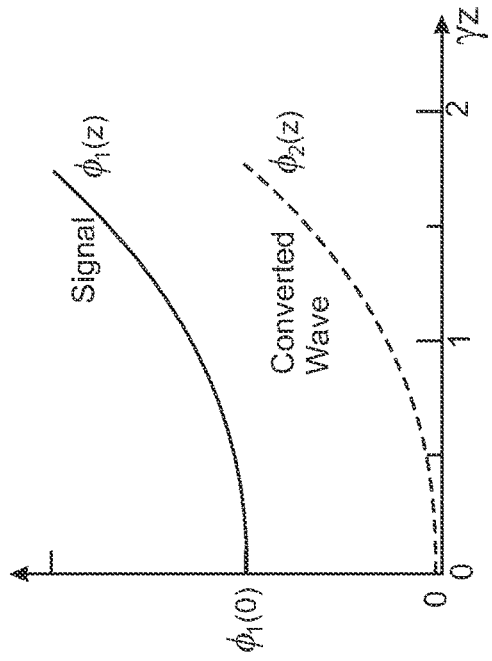
Figure 2C
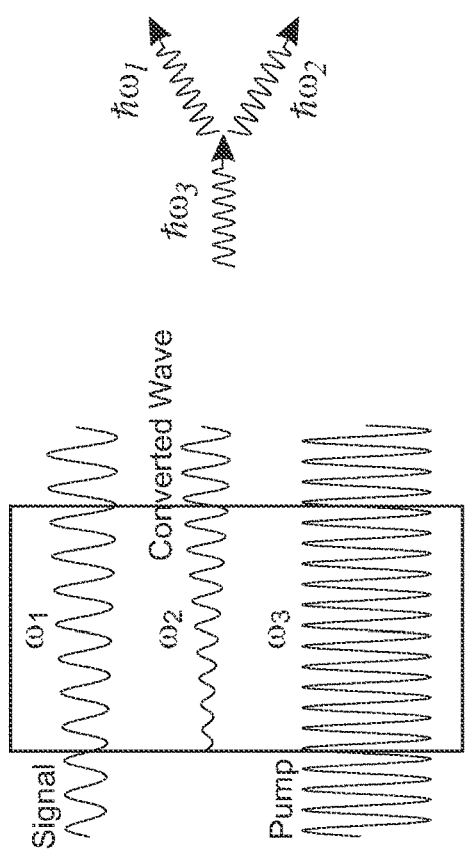
Figure 2B
Figure 2A

SOLID STATE WIDEBAND FOURIER TRANSFORM INFRARED SPECTROMETER

RELATED APPLICATIONS

This application claims the benefit of U.S. Provisional Application No. 62/079,185, filed Nov. 13, 2014, which is herein incorporated by reference in its entirety for all purposes.

FIELD OF THE INVENTION

The invention relates to infrared spectrometry, and more particularly, to Fourier transform infrared spectrometers.

BACKGROUND OF THE INVENTION

Fourier transform infrared ("FTIR") spectrometers have been in use for decades for routine chemical analysis. The FTIR concept is built on the use of an interferometer that can scan over many null and maximum points. Typically, FTIR spectrometers have used mechanical interferometers that are based on the Michelson design. These mechanical FTIR systems have demonstrated excellent performance over a wide wavelength range. In addition, some implementations of the Michelson approach have been made smaller and more rugged over time through careful design. However, a high degree of mechanical precision and cost has been required to realize such improved implementations. Also, even for the more rugged configurations, the mechanical nature of the Michelson interferometer design renders it intrinsically susceptible to misalignment and/or damage.

What is needed, therefore, is an FTIR spectrometer that can be manufactured at a reduced price and size, and that includes no moving parts.

SUMMARY OF THE INVENTION

A novel FTIR spectrometer that includes no moving parts and is less expensive to manufacture and smaller in size than conventional FTIR spectrometers based on the Michelson design includes a Mach-Zehnder interferometer that is realized in silicon. The optical path lengths of the two waveguide arms of the Mach-Zehnder interferometer are varied by changing the index of refraction of the waveguide material. In some embodiments, this is done by heating the waveguides, while in other embodiments this is accomplished by changing the carrier concentration of the Si in the waveguides. This latter approach is achieved by configuring each arm of the interferometer as either a "p-n" or "p-i-n" diode, and by changing the electrical bias conditions of the diodes. In embodiments, the optical path lengths of both of the arms are driven in opposite directions, that is, one arm is made optically longer, while the other arm is made optically shorter.

The use of silicon for the waveguide material significantly reduces the cost of manufacturing the interferometer, and in various embodiments a germanium detector is grown on the wafer, thus simplifying the packaging and reducing cost still further. Other embodiments include heterogeneous integration of an indium gallium arsenide ("InGaAs") detector diode.

The use of silicon waveguides and germanium or InGaAs detectors in various embodiments limits the operating wavelength range of the interferometer to between 1.2 μm (onset of absorption of the silicon waveguide) and 1.6 μm (absorption edge of the germanium detector) or 1.8 μm (absorption edge of an InGaAs detector). However, this small working range can be effectively expanded by up-converting longer wavelengths and down-converting shorter wavelengths so that they fall within the usable range of the interferometer/detector combination. For example, a pumping laser and a frequency mixer such as an oriented patterned gallium arsenide ("OPGaAs") or oriented patterned gallium phosphide ("OPGaP") mixer can be used to perform the up-conversion or down-conversion. Similar embodiments include frequency sum and/or difference mixers based on any of a variety of non-linear materials and methods, including periodically poled lithium niobate and zinc germanium phosphide.

In various embodiments, the pump laser is tunable over the band of interest. In some embodiments, a proper choice of laser materials allows the complete IR band to be measured, while in other embodiments the pump laser is configured to measure only a limited wavelength band where absorption lines of interest are known to exist.

In exemplary embodiments of the present invention, the spectrometer is used in a standoff configuration, wherein the sample to be measured is located at some distance from the spectrometer. Other embodiments take advantage of the small size of the invention to eliminate the $1/R^2$ loss in sensitivity that is typical of standoff sampling systems by placing the sample in a sample space provided within the spectrometer, so that the interferometer is very close to the sample being measured. The spectrometer sensitivity can be greatly increased for some of these embodiments through the use of an onboard active light source, such as a glow bar. In embodiments, the sample space can be exposed to the surrounding air to allow detection and analysis of any chemical that may be present in the ambient atmosphere.

Materials such as $LiNbO_4$ ("LN"), Zinc Germanium Phosphide ("ZGP"), and many other materials, some of which are well established and others of which are still under development, possess both transparency and high optical polarizability, and can be used in various embodiments in place of OpGaAs as an up-converting and/or down-converting medium.

The recent perfection of parallel technology in both non-linear poled materials such as OpGaAs and Si-photonics platforms is a key enabler of the present invention. In some embodiments, waveguide devices constructed of these new converter materials allow very small, commercially available cyclooctatetraene ("COT") CW laser diodes to generate the baseband spectral inputs ("BBSI") from approximately 1.2 to 1.6 microns that are required by these $Si/SiO_2$ filter devices. The CW outputs of these COT laser diodes, typically with output powers as low as 1-10 milliwatts, experience long interaction lengths in the guided modes of the waveguides, which efficiently converts, for example, the long-wave, information-rich spectral telltale signatures in the signal to the BBSI wavelength range. The relative spectral locations, widths, and intensities are thereby mapped into the converted wavelengths.

This waveguide conversion approach overcomes the natural tendency of tightly focused optical drive or pump beams to diverge, and thereby maintains the beam intensities that are required for conversion. This enables the use of simple CW pumps, which provide electrical and optical simplicity, because it eliminates the need for short-pulse pump lasers, which typically require complex and inefficient electro-optical components and accompanying high flux and peak power levels that are known to place stress on other material in the beam path.

One general aspect of the present invention is a Fourier Transform Infrared ("FTIR") Spectrometer which includes a controller, an optical signal input, an optical interferometer configured to receive an FTIR input wave from said optical signal input, said optical interferometer having at least two light paths, each of said light paths being directed through a waveguide comprising a waveguide material, all of said light paths being fixed in physical length, at least one of said light paths being variable in optical length by changing an index of refraction of the waveguide material of the light path under control of said controller, and an infrared detector, configured to receive and detect an output of the optical interferometer.

In embodiment, the interferometer is a Mach-Zehnder interferometer having two light paths. And in some of these embodiments, the optical lengths of both of the two light paths are variable in optical length under control of said controller.

In any of the above embodiments, the optical length can be variable by controlling a temperature of the waveguide material of the at least one light path. In any of the above embodiments, the optical length can be variable by controlling a carrier concentration of the waveguide material of the at least one light path.

In any of the embodiments listed above, said waveguide material can be silicon. In any of the preceding embodiments, the waveguide can be formed on a silicon wafer, and the FTIR detector can be a germanium detector that is grown on the silicon wafer.

In any of the embodiments mentioned above, the waveguide can be formed on a silicon wafer, and can include heterogeneous integration of an indium gallium arsenide (InGaAs) detector diode as the FTIR detector.

Any of the above embodiments can further include a wavelength converter, said wavelength converter comprising a pump laser and an optical mixing medium. In some of these embodiments, the optical mixing medium is OpGaAs. In other of these embodiments, optical mixing medium is LiNbO4 (LN) or Zinc Germanium Phosphide. And for any of the preceding embodiments, the optical mixing medium can be included in a mixing waveguide device, and/or the pump laser can comprise a COT CW diode laser.

Any of the above embodiments can further include a sample compartment configured to contain an FTIR test sample and to allow an infrared measurement wave to pass through the FTIR test sample, said FTIR input wave being derived from said infrared measurement wave. Embodiments further include an onboard active FTIR light source configured to generate the infrared measurement wave, and in some of these embodiments the onboard active light source is a glowbar. In various of these embodiments the sample compartment can be configured to be in gas communication with a surrounding atmosphere for analysis of the gases contained therein.

Another general aspect of the present invention is a method for performing Fourier Transform Infrared ("FTIR") spectrometry. The method includes:

a. producing an infrared wave,
b. passing the infrared wave through a sample,
c. mixing the infrared wave with an incoming pump wave,
d. producing an auxiliary wave, wherein the auxiliary wave is produced from mixing the infrared wave with the pump wave and the auxiliary wave has a wavelength within a usable range of a first waveguide, a second waveguide, and a detector, said first and second waveguides being fixed in physical length,
e. splitting the auxiliary wave into a first beam and a second beam, passing the first beam through the first waveguide, wherein the first waveguide has a first optical length,
f. passing the second beam through the second waveguide, wherein the second waveguide has a second optical length,
g. changing an index of refraction of the second waveguide, wherein changing the index of refraction creates a difference between the second optical length and the first optical length, and
h. causing the first and second beams to converge and using the detector to detect an interference between the first and second beams.

In embodiments, changing the index of refraction of the second waveguide comprises at least one of heating the second waveguide and changing a carrier concentration of the second waveguide.

And some embodiments further include changing an index of refraction of the first waveguide, such that one of the first optical length and the second optical length is increased, while the other of the first optical length and the second optical length is decreased.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

FIG. 2A is a simplified diagram illustrating the signal, pump, and converted waves that are present in the wavelength converter of FIG. 1;

FIG. 2B illustrates the momentum relationship and photon mixing between the signal, pump, and converted waves of FIG. 2A;

FIG. 2C is a graph that illustrates the relationship between the photon flux densities of the signal and converted waves, under an assumption that the pump photon-flux density is constant.

DETAILED DESCRIPTION

Figure 1:
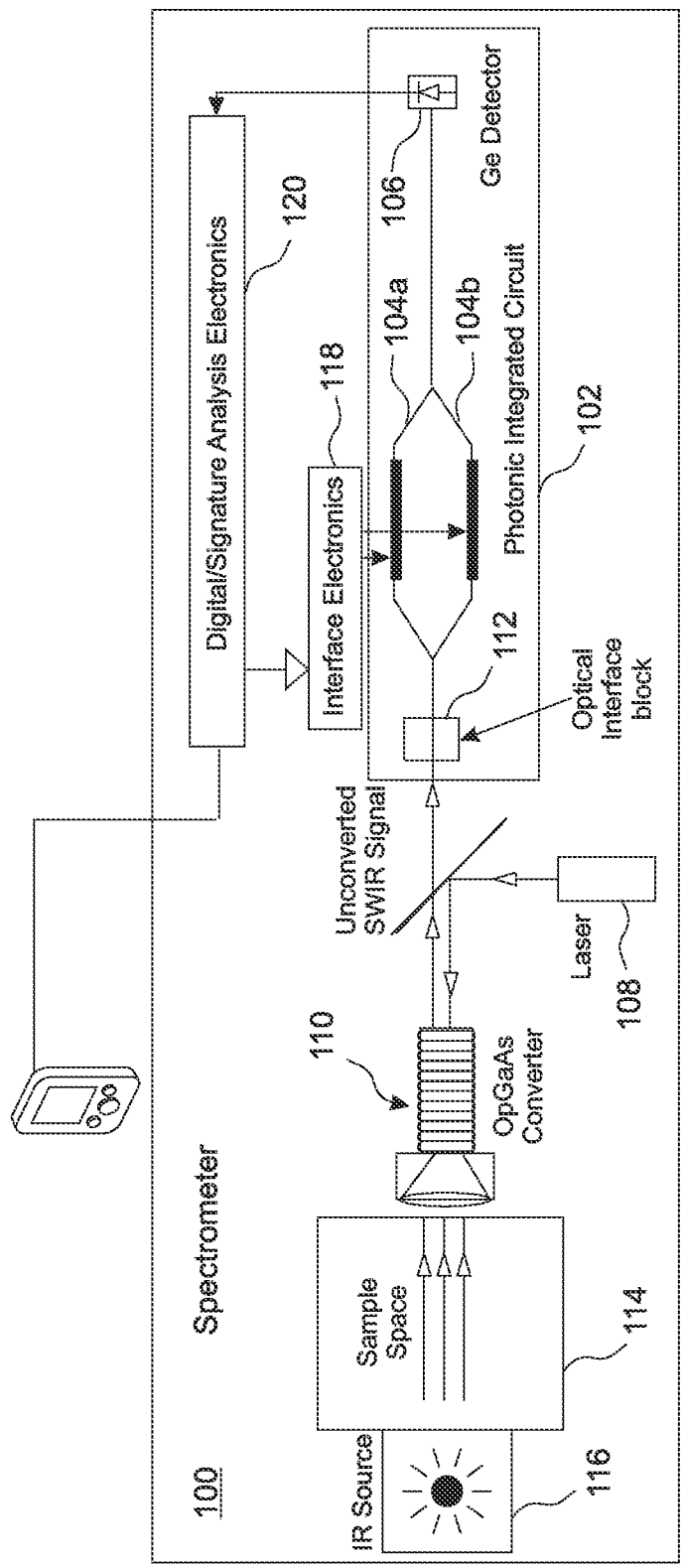
FIG. 1 is a block diagram illustrating an embodiment of the FTIR spectrometer of the present invention.

With reference to FIG. 1, a novel FTIR spectrometer 100 that is less expensive to manufacture and smaller in size than conventional FTIR spectrometers based on the Michelson design includes a Mach-Zehnder interferometer 102 that is realized in silicon and includes no moving parts. The optical path lengths of the two waveguide arms 104a, 104b of the interferometer 102 are varied under control of interface electronics 118 by changing the index of refraction of the waveguide material. In some embodiments, this is done by heating the waveguides, while in other embodiments this is accomplished by changing the carrier concentration of the Si in the waveguides. This latter approach is achieved by configuring each arm 104 as either a "p-n" or "p-i-n" diode and by changing the electrical bias conditions of the diodes. In embodiments, the optical path lengths of both of the arms 104 are driven in opposite directions; that is, one arm 104a is made optically longer, while the other arm 104b is made optically shorter.

The use of silicon for the waveguide material significantly reduces the cost of manufacturing the interferometer 102. In embodiments, a typical 6" silicon wafer can yield several hundred such devices. In various embodiments, a germanium detector 106 is grown on the wafer, thus simplifying the packaging and reducing cost still further. Other embodiments include heterogeneous integration of an indium gallium arsenide ("InGaAs") detector diode.

In the embodiment of FIG. 1, the spectrometer 100 further includes a control system 120 that drives the interface electronics and analyzes the signals received from the germanium detector 106.

The use of silicon waveguides 104 and germanium detectors 106 or InGaAs detectors in various embodiments limits the operating wavelength range of the interferometer 102 to between 1.2 µm (onset of absorption of the silicon waveguide) and 1.6 µm (absorption edge of the germanium detector) or 1.8 µm (absorption edge of an InGaAs detector). However, this small working range can be expanded by up-converting longer wavelengths and down-converting shorter wavelengths so that they fall within the useful range of the interferometer/detector combination. In the embodiment of FIG. 1, this is accomplished by a pumping laser 108 and an oriented patterned gallium arsenide ("OPGaAs") frequency difference mixer 110. Similar embodiments include frequency sum and/or difference mixers based on any of a variety of non-linear materials and methods, including periodically poled lithium niobate, zinc germanium phosphide, and oriented patterned gallium phosphide ("OPGaP").

In the embodiment of FIG. 1, an optical interface block 112 couples the energy from the wavelength converter 110 into the very small Si waveguide 104. In some embodiments, this is accomplished by direct focusing of the energy onto the end of the waveguide 104. In other embodiments, a grating is used to couple the energy from the converter 110 at an incident angle to the end of the waveguide 104. In still other embodiments, a fiber optic lead is used to guide the energy to the waveguide 104 through the use of tapered fibers or ball lenses.

In various embodiments, the laser 108 is configured to be tuned to cover the band of interest. In some embodiments, a proper choice of laser materials allows the complete IR band to be measured, while in other embodiments the laser is configured to measure only a limited wavelength band where absorption lines of interest are known to exist.

In exemplary embodiments of the present invention, the spectrometer is used in a standoff configuration, wherein the sample to be measured is located at some distance from the spectrometer. With reference to FIG. 1, other embodiments take advantage of the small size of the invention to eliminate the $1/R^2$ loss in sensitivity that is typical of standoff sampling systems by placing the sample in a sample space 114 provided within the spectrometer 100, so that the interferometer 102 is very close to the sample being measured 114. The spectrometer sensitivity can be greatly increased for some of these embodiments through the use of an onboard active light source 116, such as a glow bar. In embodiments, the sample space 114 can be exposed to the surrounding air to allow detection and analysis of any chemical that may be present in the ambient atmosphere.

Materials such as $LiNbO_4$ (LN), Zinc Germanium Phosphide (ZGP), and many other materials, some of which are well established and others of which are still under development, possess both transparency and high optical polarizability and can be used in various embodiments in place of OpGaAs 110 as an up-converting and/or down-converting medium. Through non-linear optical mixing, a desired IR band can thereby be translated so that it falls with the usable range of the Si waveguides 104 and the integrated Ge detectors 106, thereby enabling them to detect a broader range of compounds at their fundamental ID wavelengths, where the distinguishing spectral features are stronger.

As noted above, the incoming signal can be mixed with an on-board 108 laser using either Difference Frequency Mixing ("DFM"), or Sum Frequency Mixing ("SFM"). Either technique is usable, but for simplicity only DFM is described herein. One of skill in the art will readily perceive how SFM can be applied in a similar manner.

The recent perfection of parallel technology in both non-linear poled materials such as OpGaAs and Si-photonics platforms is a key enabler of the present invention. With reference to FIG. 2A, the Difference Frequency Mixer (DFM) approach uses three-wave mixing in a nonlinear material to provide optical gain. The process is governed by three coupled energy exchange equations with the waves identified as follows:

The first wave, $\omega 1$, is the input signal, and is incident on the crystal 110 with a small input intensity I1(0). A second wave, $\omega 3$, the pump, is an intense wave that provides power to the mixer 110. The newly generated converted wave, $\omega 2$, is an auxiliary wave created by this interaction process. In the DFM case, $\omega 2$ represents the up-converted frequency suitable for injection into the silicon waveguide 104. Energy conversion dictates that $$\omega 2 = \omega 3 - \omega 1 \tag{1}$$

The coherent growth of the preferred optical frequencies along the axis of propagation is assured by the matching of the different frequency fields with dispersion invoked momentum matching, according to $$k3 = k1 + k2 \tag{2}$$

Which can be written $$\hbar \omega 3 = \hbar \omega 1 + \hbar \omega 2 \tag{3}$$

as illustrated in FIG. 2B. DFM has the additional merit of providing gain as long as the applied pump intensity is sufficiently high. Small signal conversion efficiency in the mid-infrared wavelength range has been shown to reach 175% v with 150 mW of laser diode pump energy.

The weak input beams $\omega 1$ are collected and guided into the converter material volume 110 and mixed with the output of the driving pump laser 108. The high intensity of the pump beam $\omega 3$, in conjunction with the input beam $\omega 1$, deforms the charge clouds surrounding the molecules of the converter material. The beat of these two beams $\omega 1$, $\omega 3$ drives the high order wave propagation, such that new electric fields are generated. Due to the natural or engineered dispersion of the converter material, as illustrated in FIG. 2C, a narrow portion of these harmonic polarization fields matches the phase speeds $\phi 1$, $\phi 2$ of the two original beams. This causes both the signal and converted waves to grow as individual pump photons "split" into a modified signal beam and a newly generated, converted beam.

Figure 3:
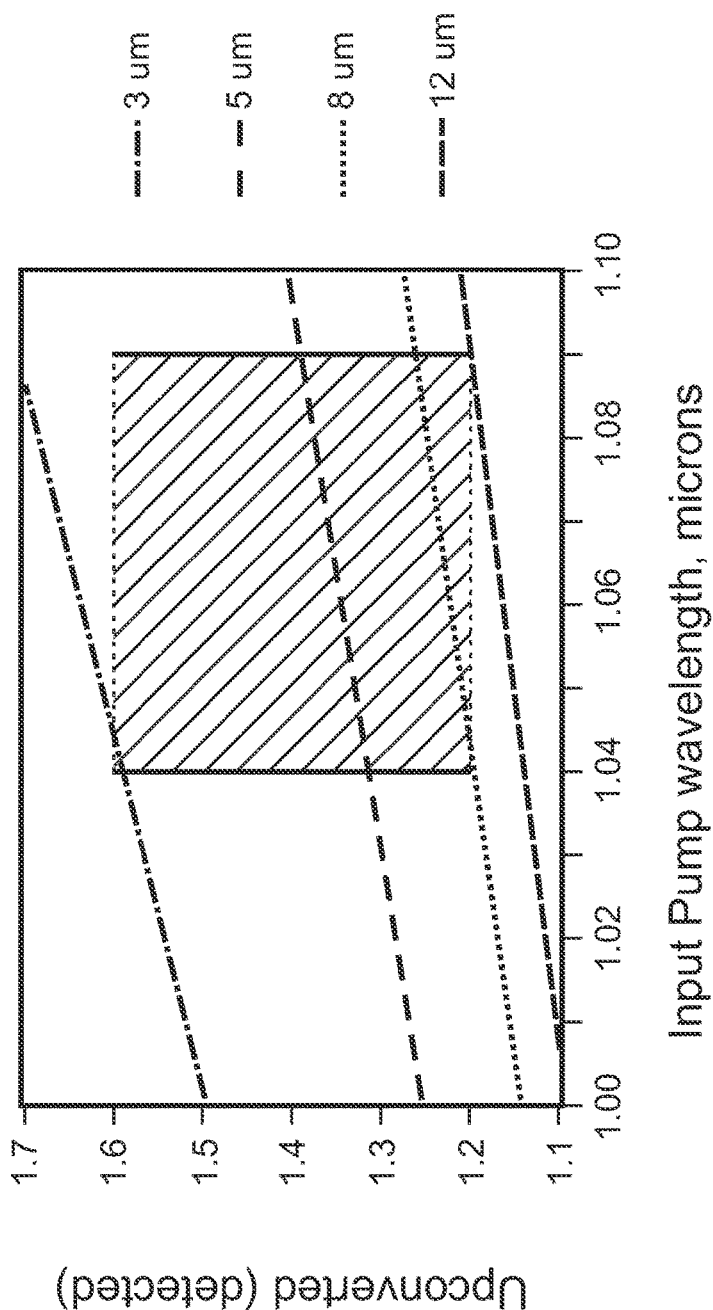
FIG. 3 is a graph that illustrates the difference frequency mixing pump wavelength variance that is required to convert a signal in the mid-infrared input spectrum and the long wave infra-red input spectrum into a wavelength band that is compatible with the silicon waveguides and germanium detector used in embodiments of the present invention.

FIG. 3 depicts the range of mid wave and long wave infrared inputs (four dashed curves) and their resulting converted wavelengths (vertical axis) as a function of the pump wavelength, (horizontal axis) for an exemplary embodiment. It can be seen from the figure that the two bands representing the signature-rich spectral bands which overlap with good atmospheric transmission, namely the 3-5 um and the 8-12 um bands, are up-converted by the OpGaAs converter 110 into the vertical limits of the cross-hatched box region in the figure, which is demarked on the vertical axis as 1.2 to 1.6 um. The straight vertical lines on the left and right sides of the box define the pump laser central wavelengths required to achieve this converted output.

As can be seen from the figure, by varying the central wavelength of the pump laser 108, the two aforementioned spectral inputs can be converted into the detector's spectral response window by varying the pump wavelength from 1.04 to 1.09 um. In some embodiments, cyclooctatetraene ("COT") CW laser diodes are used to meet these requirements, while in other embodiments a broadband laser source such as a CW laser diode pumped broadband laser having this range of spectral output is used.

Additionally, in some embodiments waveguide devices constructed of these new converter materials allow very small, commercially available COT laser diodes to generate the baseband spectral inputs ("BBSI") from approximately 1.2 to 1.6 microns that are required by these $Si/SiO_2$ filter devices. The CW outputs of these COT laser diodes, typically with output powers as low as 1-10 milliwatts, experience long interaction lengths in the guided modes of the waveguides, which efficiently converts, for example, the long-wave, information-rich spectral telltale signatures in the signal to the BBSI wavelength range. The relative spectral locations, widths, and intensities are thereby mapped into the converted wavelengths.

This waveguide conversion approach overcomes the natural tendency of tightly focused optical drive or pump beams to diverge, and thereby maintains the beam intensities that are required for conversion. This enables the use of simple CW pumps, which provide electrical and optical simplicity, because it eliminates the need for short-pulse pump lasers, which typically require complex and inefficient electro-optical components and accompanying high flux and peak power levels that are known to place stress on other material in the beam path.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application.

This specification is not intended to be exhaustive. Although the present application is shown in a limited number of forms, the scope of the invention is not limited to just these forms, but is amenable to various changes and modifications without departing from the spirit thereof. One or ordinary skill in the art should appreciate after learning the teachings related to the claimed subject matter contained in the foregoing description that many modifications and variations are possible in light of this disclosure. Accordingly, the claimed subject matter includes any combination of the above-described elements in all possible variations thereof, unless otherwise indicated herein or otherwise clearly contradicted by context. In particular, the limitations presented in dependent claims below can be combined with their corresponding independent claims in any number and in any order without departing from the scope of this disclosure, unless the dependent claims are logically incompatible with each other.

We claim:

1. A Fourier Transform Infrared ("FTIR") Spectrometer, comprising:
   a controller;
   an optical signal input;
   an optical interferometer configured to receive an FTIR input wave from said optical signal input, said optical interferometer having at least two light paths, each of said light paths being directed through a waveguide comprising a waveguide material, all of said light paths being fixed in physical length, at least one of said light paths being configured as a diode and being variable in optical length by changing an electrical bias condition of the diode under control of said controller; and
   an infrared detector, configured to receive and detect an output of the optical interferometer;
   said controller being further configured to analyze the detected output of the optical interferometer, and determine therefrom a Fourier transform infrared spectrum of the FTIR input wave.

2. The FTIR spectrometer of claim 1, wherein the interferometer is a Mach-Zehnder interferometer having two light paths.

3. The FTIR spectrometer of claim 2, wherein the optical lengths of both of the two light paths are variable in optical length under control of said controller.

4. The FTIR spectrometer of claim 1, wherein said waveguide material is silicon.

5. The FTIR spectrometer of claim 1, wherein the waveguide is formed on a silicon wafer, and the FTIR detector is a germanium detector that is grown on the silicon wafer.

6. The FTIR spectrometer of claim 1, wherein the waveguide is formed on a silicon wafer, and includes heterogeneous integration of an indium gallium arsenide (InGaAs) detector diode as the FTIR detector.

7. The FTIR spectrometer of claim 1, further comprising a wavelength converter, said wavelength converter comprising a pump laser and an optical mixing medium.

8. The FTIR spectrometer of claim 7, wherein the optical mixing medium is OpGaAs.

9. The FTIR spectrometer of claim 7, wherein optical mixing medium is $LiNbO_4$ (LN) or Zinc Germanium Phosphide.

10. The FTIR spectrometer of claim 7, wherein the optical mixing medium is included in a mixing waveguide device.

11. The FTIR spectrometer of claim 7, wherein the pump laser comprises a COT CW diode laser.

12. The FTIR spectrometer of claim 1, further comprising a sample compartment configured to contain an FTIR test sample and to allow an infrared measurement wave to pass through the FTIR test sample, said FTIR input wave being derived from said infrared measurement wave.

13. The FTIR spectrometer of claim 12, further comprising an onboard active FTIR light source configured to generate the infrared measurement wave.

14. The FTIR spectrometer of claim 13, wherein the onboard active light source is a glowbar.

15. The FTIR spectrometer of claim 12, wherein the sample compartment can be configured to be in gas communication with a surrounding atmosphere for analysis of the gases contained therein.

16. A method for performing Fourier Transform Infrared ("FTIR") spectrometry comprising the steps of:
   producing an infrared wave;

passing the infrared wave through a sample;
mixing the infrared wave with an incoming pump wave;
producing an auxiliary wave, wherein the auxiliary wave is produced from mixing the infrared wave with the pump wave, wherein the auxiliary wave has a wavelength within a usable range of a first waveguide, a second waveguide, and a detector, said first and second waveguides being fixed in physical length, the second waveguide being configured as a diode;
splitting the auxiliary wave into a first beam and a second beam;
passing the first beam through the first waveguide, wherein the first waveguide has a first optical length;
passing the second beam through the second waveguide, wherein the second waveguide has a second optical length;
varying an index of refraction of the second waveguide by changing an electrical bias condition of the diode under control of a controller, wherein varying the index of refraction of the second waveguide controls and varies a difference between the second optical length and the first optical length;
causing the first and second beams to converge;
using the detector to detect an interference between the first and second beams as a function of the difference between the second optical length and the first optical length; and
determining from the detected interference a Fourier transform infra-red spectrum of the sample.

17. The method of claim 16, further comprising changing an index of refraction of the first waveguide, such that one of the first optical length and the second optical length is increased, while the other of the first optical length and the second optical length is decreased.

\* \* \* \* \*